US006804001B1

(12) United States Patent
Leroux

(10) Patent No.: US 6,804,001 B1
(45) Date of Patent: Oct. 12, 2004

(54) DEVICE FOR MEASURING SPATIAL DISTRIBUTION OF THE SPECTRAL EMISSION OF AN OBJECT

(75) Inventor: Thierry Leroux, Ouistreham (FR)

(73) Assignee: Eldim, Herouville St Clair (FR)

( * ) Notice: Subject to any disclaimer, the term of this patent is extended or adjusted under 35 U.S.C. 154(b) by 168 days.

(21) Appl. No.: 10/110,775

(22) PCT Filed: Oct. 25, 2000

(86) PCT No.: PCT/FR00/02965

§ 371 (c)(1),
(2), (4) Date: Apr. 26, 2002

(87) PCT Pub. No.: WO01/31303

PCT Pub. Date: May 3, 2001

(30) Foreign Application Priority Data

Oct. 26, 1999 (FR) .............................. 99 13342

(51) Int. Cl.[7] .................................................. G01J 3/28
(52) U.S. Cl. ........................................ 356/326; 356/328
(58) Field of Search ................................. 356/326, 328, 356/334; 250/226

(56) References Cited

U.S. PATENT DOCUMENTS 5,724,135 A * 3/1998 Bernhardt .................... 356/328

5,880,845 A * 3/1999 Leroux .......................... 356/73

FOREIGN PATENT DOCUMENTS

| EP | 0 286 529 | 4/1988 |
| FR | 2 729 220 | 1/1995 |
| FR | 2 749 388 | 12/1997 |

OTHER PUBLICATIONS

Saleh & Kanglia: "The Fourier scope: an analytical Instrument for measuring LCD viewing–angle characteristics" Journal of the Society for Information Display, vol. 4, No. 1, pp. 33–39 04/96.

* cited by examiner

Primary Examiner—F. L. Evans
Assistant Examiner—Kara Geisel
(74) Attorney, Agent, or Firm—Oblon, Spivak, McClelland, Maier & Neustadt, P.C.

(57) ABSTRACT

A device for measuring the space distribution of the spectral emission of an object. The device includes a first lens forming in its Fourier plane an image constituting the optical Fourier transform of a zone of the object, a second lens, a diaphragm conjugated optically with the zone by the first and second lenses, a mechanism for selecting a rectilinear portion of the image, a mechanism for dispersion of the light corresponding to this portion, and a sensor receiving the dispersed light. The spectral response of the zone, for each point of the portion, is determined by signals from the sensor. The device is applicable in particular to display screens.

12 Claims, 6 Drawing Sheets

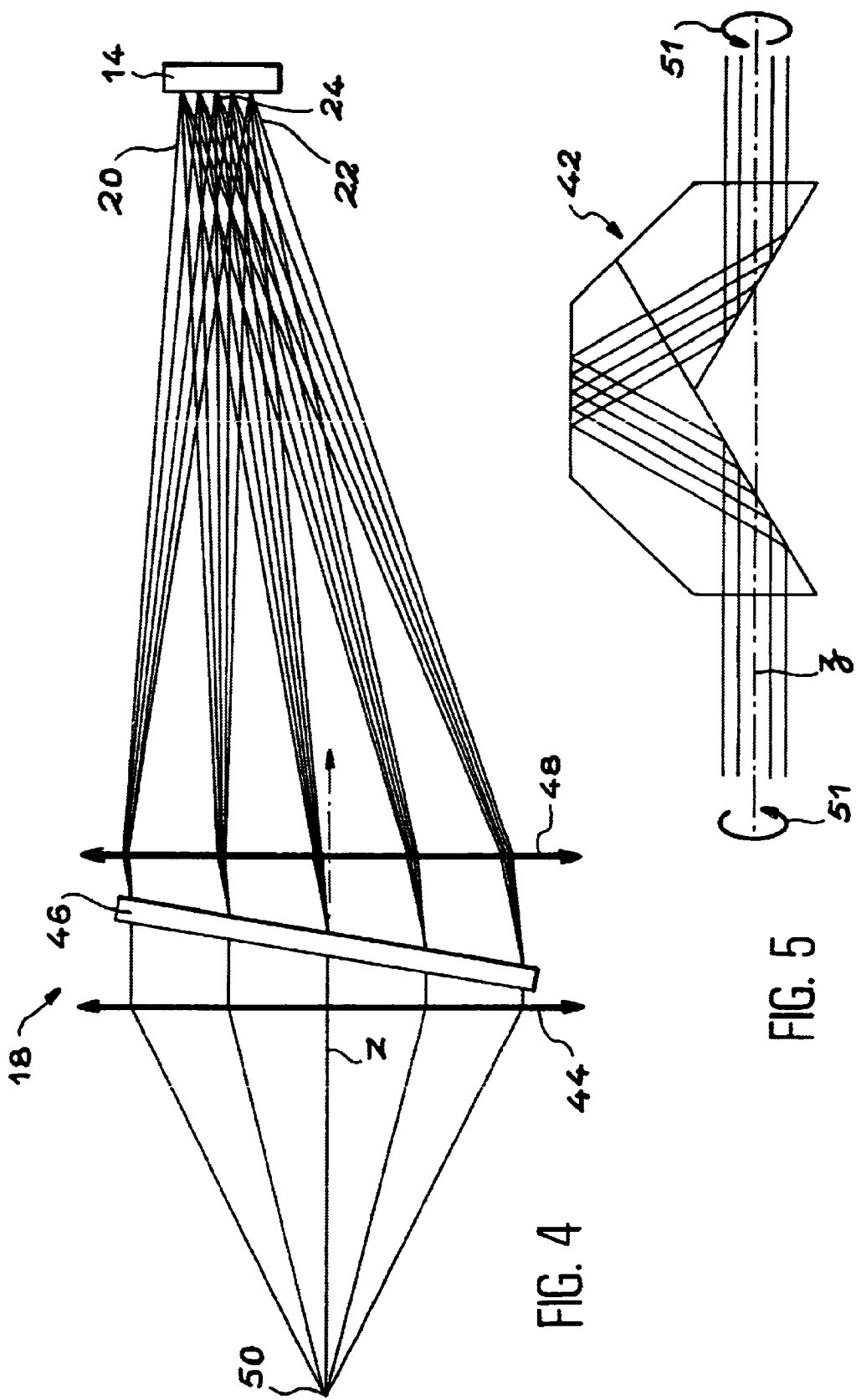

DEVICE FOR MEASURING SPATIAL DISTRIBUTION OF THE SPECTRAL EMISSION OF AN OBJECT

TECHNICAL FIELD

The present invention relates to a device for measuring the space distribution of the spectral emission of an object.

It applies in particular to objects such as, for example, projection screens, cathode ray tubes, lighting devices, flat display screens such as liquid crystal screens, plasma screens, electroluminescent screens and microtip screens, as well as reflecting surfaces.

STATE OF PRIOR ART

Several techniques are already known for measuring the calorimetric specifications of the emission or reflection of light by various objects (for example those mentioned above) as a function of the angle of observation.

Reference can be made to the following documents on this subject:

[1] EP 0 286 529 A
[2] FR 2 729 220 A
[3] FR 2 749 388 A

In particular an electromechanical technique is known which consists of moving measuring equipment, such as a photometer, around an object which one wishes to measure. On this subject, reference can be made, for example, to document [1] and in particular to FIGS. 2a, 2b and 3 of this document [1].

This known technique presents many inconveniences.

In particular, the measurement is carried out by sampling. Only the positions chosen are measured and no information is known about the luminance in the intermediary positions or angles. No certitude exists about the luminance value apart from that at the measured points.

In addition, the measurements, of duration $T_0$, are carried out in series, one after the other. If a large number of points N are to be measured in order to be able to obtain a maximum of information, the complete measurement of the object takes a time $NxT_0$.

Another technique is known which uses a Fourier optic associated with an array sensor of the CCD type or other. On this subject, reference should be made, for example, to document [3] and in particular to FIG. 1 of this document [3].

This other known technique consists of obtaining, in one go, the space distribution of the light emitted or reflected on this matrix sensor by an object to be measured. The different points of the image correspond to the measurements obtained for the emission specifications of the object to be measured, at different angles.

The principal advantages of this other technique are the following:

The speed of measurement is higher. In fact the measurement of duration $T_1$ does not depend on, or depends little on, the number of points measured.

All the information is available.

There is no risk that a detail of the angular distribution of luminance escapes being measured.

An integration (summation) of the overall values obtained gives with certainty a value for the luminous flux emitted by the object.

Nonetheless, a serious inconvenience has become apparent during usage of this other known technique. In fact, (and referring to documents [1] and [2]), the measurement of luminous flux is carried out without reference to the distribution by wavelength of the collected light. This can be restrictive if one is trying to obtain spectral variations in function of the angle of observation, in colorimetry where it is sometimes complicated and always imprecise to calculate the colorimetric co-ordinates without knowing the spectral distribution of the light, and in reflectometry where it is indispensable to know the spectrum of the light source used to illuminate an object in order to evaluate the capacity of the object to reflect any particular wavelength.

DESCRIPTION OF THE INVENTION

The aim of the present invention is to remedy these inconveniences.

Its objective is a device which combines the advantages of the technique described in document [3], advantages which have been seen above, with the advantages of spectral measurement.

Certainly, one could envisage (as do documents [2] and [3]), placing a series of selective filters in the path of the luminous signal, making it possible to select a range of wavelengths.

Nonetheless, given that the spread of the visible spectrum is 340 nm (since this visible spectrum ranges from 380 nm to 720 nm) and that the resolution needed for photometric measurements is of the order of 4 nm, 85 successive filters (and 85 successive measurements) would be necessary. Such a technique would therefore lead to long measuring times.

Furthermore, the setting up of 85 filters in the path of a luminous signal is not simple and the cost of these 85 filters is not negligible, since the manufacture of filters with a 4 nm bandpass is especially delicate.

Nevertheless one could think of using a restricted number of filters, each filter with a 10 nm bandpass. But then there would be only 34 filters and the precision of the measuring device would be lowered.

The device which is the subject of the invention combines the advantages indicated above without presenting the inconveniences which have just been described concerning this utilisation of a series of selective filters.

To be precise, this present invention has the aim of a device for measuring the space distribution of the spectral emission of a measurement zone of an object, this device being characterised in that it comprises:

a first lens envisaged to form, in the Fourier plane of this first lens, a first image constituting the optical Fourier transform of the zone of measurement, a first diaphragm a second lens set between the first lens and the first diaphragm and co-operating with this first lens so that the opening of the first diaphragm shall be conjugated optically with the measuring zone by the first and second lenses and that the measurement zone, when it is observed through the first diaphragm, has an apparent surface approximately independent from the direction of observation, the first and second lenses having a common optical axis which constitutes the optical axis of the device, means of selection of a rectilinear portion of the first image following a direction of selection, means of light dispersion, envisaged to disperse the light corresponding to the selected portion of the first image, a bidimensional image sensor, envisaged to receive the light thus dispersed and to provide signals representative of this dispersed light, and means of treatment of these signals, able to determine the spectral response of the measurement zone for each point of the rectilinear portion of the first image.

Preferably, the first diaphragm has a circular opening.

Preferably also, the means of dispersion are able to disperse the light following a dispersion direction which is perpendicular to the direction of selection.

According to a preferred embodiment of the device which is the subject of the invention, the means of selection comprise a rectilinear slit which is formed through a material opaque to the light issued from the object.

According to a preferred embodiment of the device which is the subject of the invention, the direction of selection passes along the optical axis of the device.

In this case, the device which is the subject of the invention can also comprise means of rotation of the object around the optical axis of the device. This makes it possible to measure the specifications of the measurement zone for different values of the azimuth φ.

Alternatively, the device which is the subject of the invention can also comprise means for displacing the means of selection, in such a way that the selection direction scans the first image, the means of selection thus selecting successive rectilinear portions of this first image.

In this case, according to a special embodiment of the invention, the means of selection comprise a rectilinear slit which is made through a material which is opaque to the light issuing from the object and which defines the direction of selection, this slit passing along the optical axis of the device, and the means of displacement are the means of rotation of the slit around this optical axis and the means of dispersion are able to disperse the light following a dispersion direction which is maintained perpendicular to the direction of selection and thus to the slit.

Also in this case, according to another particular embodiment, the means of selection comprise a rectilinear slit which is made through a material which is opaque to the light issuing from the object and which defines the direction of selection, this slit passing along the optical axis of the device, and the means of displacement are means of rotation of the slit around this optical axis and the device also comprises de-rotator means which are set between the slit and the means of dispersion and are envisaged to maintain constant the orientation of the dispersed light received by the sensor.

The device which is the subject of the invention can also comprise a luminous source and semi-reflecting means envisaged to reflect the light emitted by this luminous source towards the object so as to illuminate a zone of the latter containing the zone to be measured and to let pass the light issuing from this measurement zone thus illuminated and which is directed towards the first diaphragm.

In this case, according to a first particular embodiment, the semi-reflecting means are set between the second lens and the first diaphragm and the device comprises in addition:

a second diaphragm whose opening defines the illuminated zone, this opening of the second diaphragm being conjugated optically with the zone illuminated by the ensemble formed by the first and second lenses, and a third lens, the luminous source being set in a plane which is conjugated optically with the Fourier plane of the first lens by the ensemble formed by the second and third lenses.

In this case as well, according to a second particular embodiment, the semi-reflecting means are set between the first lens and the second lens and the device also comprises:

third dad fourth lenses, and a second diaphragm whose opening defines the illuminated zone, this opening of the second diaphragm being conjugated optically with the illuminated zone by the ensemble formed by the first and fourth lenses, the luminous source being set in a plane which is conjugated optically with the Fourier plane of the first lens by an ensemble formed by the third and fourth lenses.

BRIEF DESCRIPTION OF THE DRAWINGS

The present invention will be better understood by reading the description of examples of embodiment given below, purely indicative and non-limiting, with reference to the drawings in the appendices in which:

FIG. 4 illustrates diagrammatically an example of a means of dispersion of light which can be used in the invention, FIG. 5 illustrates diagrammatically an example of de-rotator means which can be used in the invention.

DETAILED DESCRIPTION OF PARTICULAR EMBODIMENTS

Figure 1:
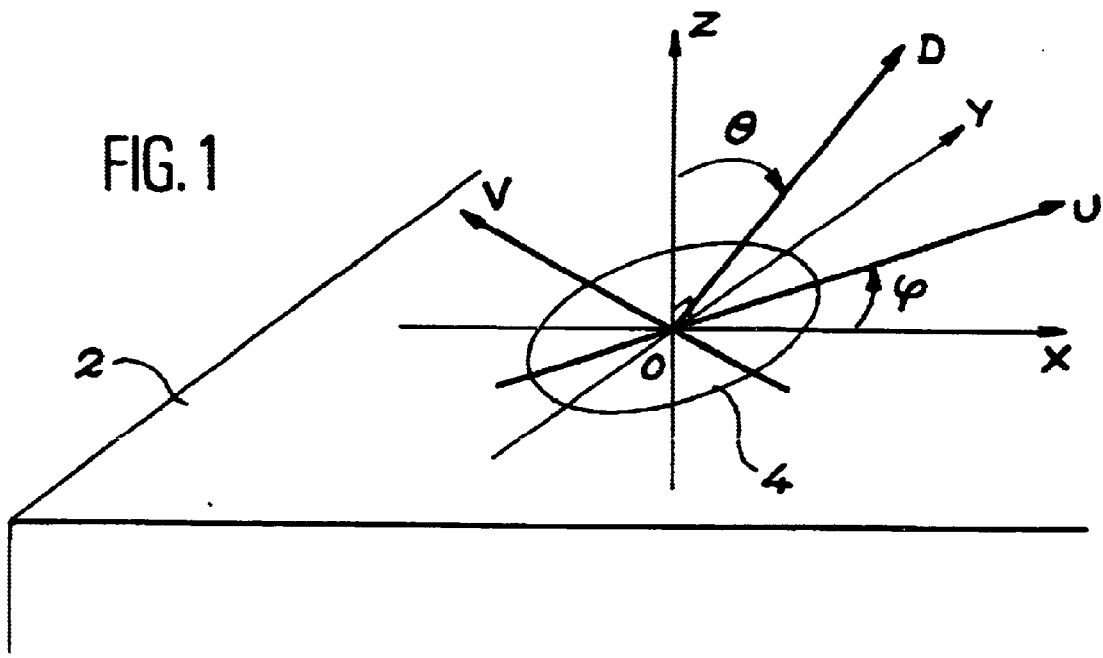
FIG. 1 is a diagrammatic view of a zone of an object which is to be measured with a device conforming to the invention following a determined observation plane.

In FIG. 1, one sees an object 2, for example a display screen which has been switched on (or a projection screen illuminated by means not shown).

One wishes to measure the space distribution of the spectral emission of a zone 4 of the surface of the object 2, called "measurement zone".

In order to do this, one uses a device conforming with the invention in which one only sees the optical axis Z on FIG. 1. The measurement zone 4 is placed facing this device, in such a way that the optical axis Z of the latter is perpendicular to the surface of the object and passes through the centre O of the measurement zone 4. In FIG. 1 one also sees two other axes X and Y and the surface of the object 2, such that the OXYZ trihedron is a direct tri-rectangular trihedron.

In order to measure another zone of the object 2 it suffices to displace this object relative to the device (or the inverse) in such a way as to place this other zone facing the device.

In FIG. 1 one can also see an axis U of the OXY plane. This axis U defines, with the axis Z, an observation plane of the measurement zone 4. An observation axis D has also been represented included in this observation plane.

The angle between the axis X and the axis U is noted as φ and is called "azimuth". The angle between the axis Z and the axis D (forming an observation direction) is noted as θ. On FIG. 1 an axis V of the surface of the object can also be seen, which is perpendicular to the axis U.

Figure 2A:
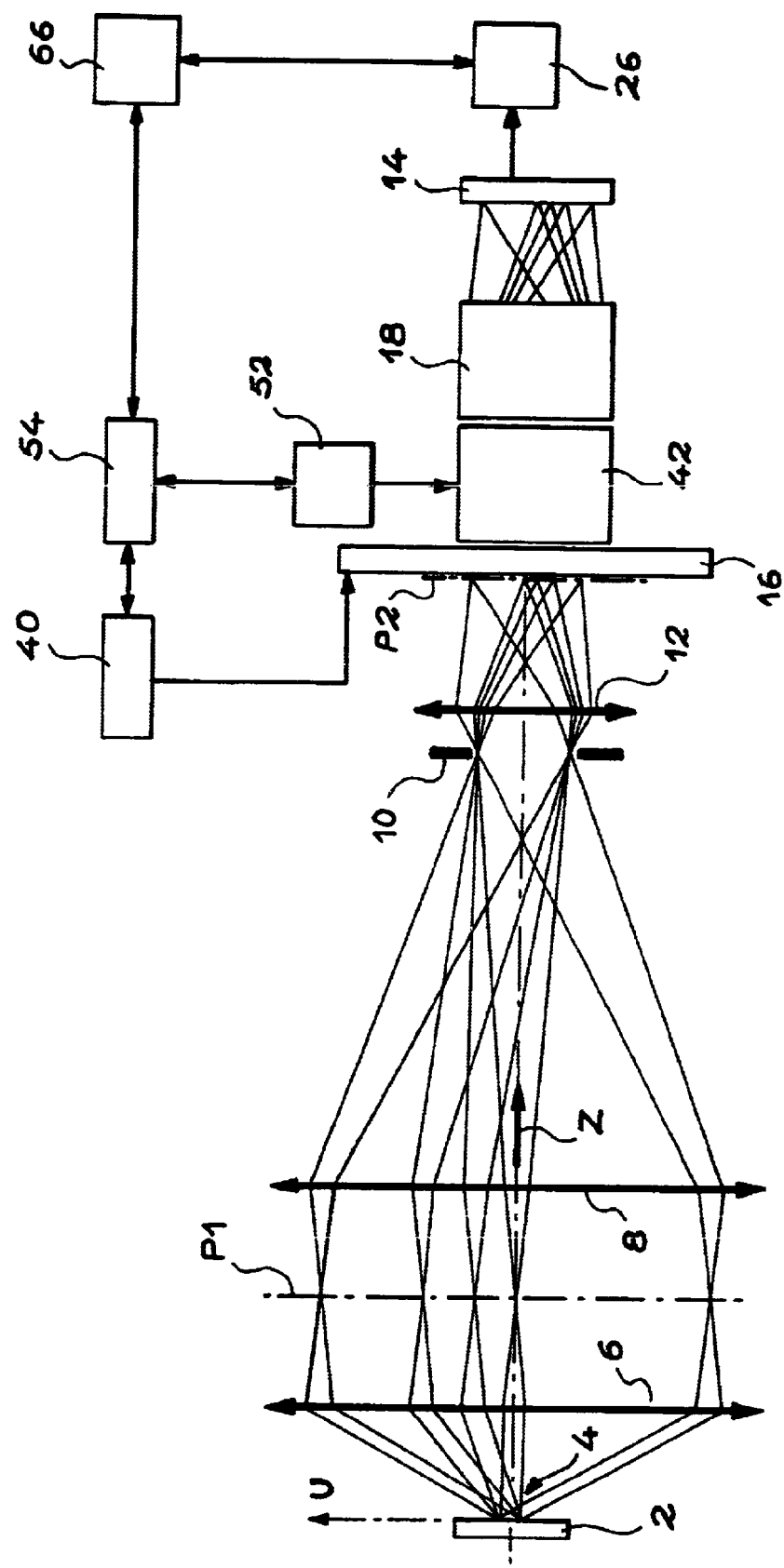
FIG. 2A is a diagrammatic view of a particular embodiment of the device which is the subject of the invention in this observation plane.

An example of the device conforming to the invention, making it possible to measure zone 4 of FIG. 1, is represented diagrammatically in FIG. 2A in the observation plane defined by the axes U and Z, axis Z being, as one has seen, the optical axis of this device. This observation plane is thus the plane of the straight section of zone 4 being analysed.

The device of FIG. 2A comprises an angular-planar conversion assembly comprising successively a first convergent lens 6, a second convergent lens 8 or field objective and a diaphragm 10.

Concerning such an angular-planar conversion assembly, one should refer to documents [1] to [3], in particular document [3].

The surface of the object 2 being analysed is preferably in the object focal plane of the first convergent lens 6. Moreover, this lens 6, in its Fourier plane P1, carries out the optical Fourier transform of the measurement zone 4.

This Fourier transform makes it possible to represent, in a plane form, the angular distribution of the luminous flux emitted by object 2 in the measurement zone 4. This image of angular distribution is thus formed in plane P1.

The second convergent lens 8 is placed in the proximity of the Fourier plane P1 and makes it possible, in association with lens 6, to ensure the optical conjugation between the measurement zone 4 and the diaphragm 10 or, more exactly, the opening of this diaphragm.

The angular-planar conversion assembly formed by lenses 6 and 8 and the diaphragm 10 is such that the apparent surface of the measurement zone 4, when observed through the diaphragm, for any observation direction D (indicated by an angle θ) of any observation plane whatsoever, has an approximately constant value $S_0$. In particular, this apparent surface has the value $S_0$ when observed along the optical axis Z.

The projection of this apparent surface on the XOY plane of the measurement zone 4 thus varies approximately as $S_0/\cos \theta$.

The diaphragm 10 whose size and shape determine those of the measurement zone following the optical axis Z is advantageously of a circular shape. The measurement zone is then elliptic in shape, if one calls the small axis of this zone $D_0$, its big axis then has an approximate value of $D_0/\cos \theta$. This big axis is in this case contained in the plane formed by the optical axis Z and the direction of measurement D.

As it has been seen, this diaphragm is conjugated optically with zone 4 by means of lenses 6 and 8.

During manufacture of the device of FIG. 2A, one chooses the magnification (relation between the size of the opening of diaphragm 10 and the size of the measurement zone 4) which one wishes to introduce at the time of this conjugation.

The device of FIG. 2A also comprises another lens 12, or relay objective, which is placed after diaphragm 10, preferably close to the latter, in such a way as to transport the image of the Fourier transform, which is in plane P1, into a second plane P2. This transformation can be accompanied by a scaling in such a way as to reduce the image found in plane P1 to a size compatible with an image sensor 14 which the device of FIG. 2A comprises, and with the rest of the optical means of this device.

The device of FIG. 2A also comprises means of selection of a straight section, or portion, of the image which is present in the Fourier plane P1.

In the example under consideration, this section or portion is advantageously arranged in such a way as to pass along the optical axis Z of the device. In this case the means of selection produce a selection with constant azimuth (angle φ of FIG. 1).

These means of selection can be placed indifferently in the plane P1 or the plane P2.

In the example under consideration, as selection means, one uses a rectilinear slit 16 formed out of an opaque material. In this example, the slit 16 is in the plane formed by the axes U and Z and it is parallel to the axis U.

The device of FIG. 2A also comprises means 18 for light dispersion comprising, for example, a diffraction grating used in transmission or in reflection or a prism. These means of dispersion are placed after the plane P2. In addition, these means of dispersion are advantageously placed in such a way that the direction of dispersion is perpendicular to the direction of selection (direction of the slit 16).

Figure 2B:
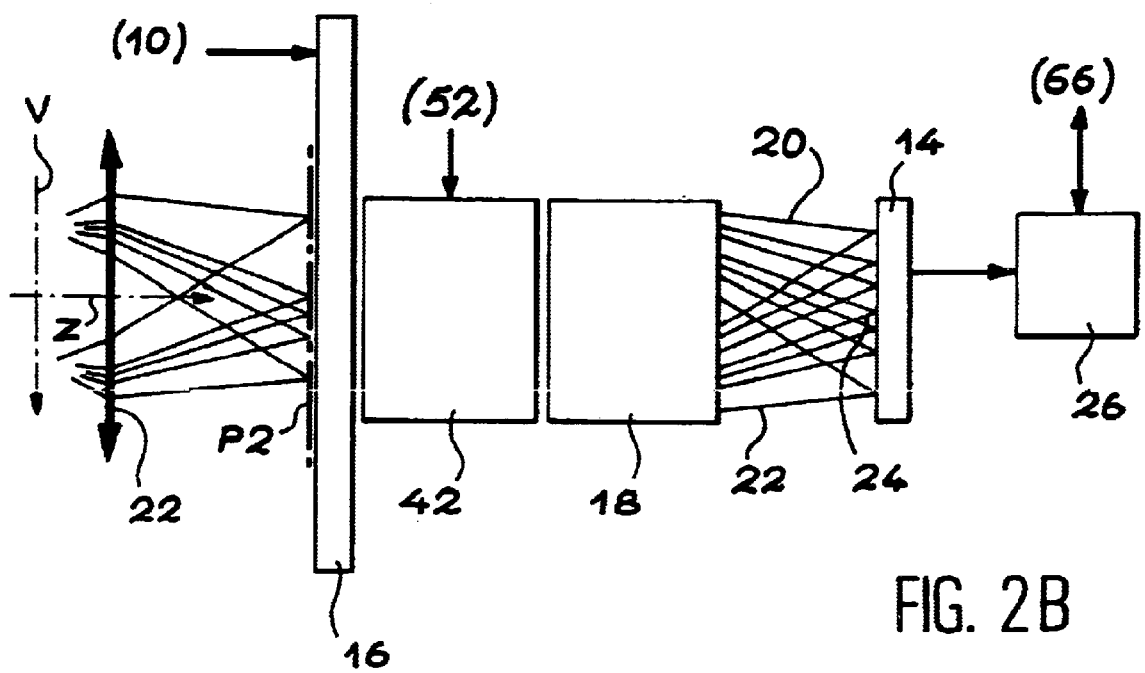
FIG. 2B is a diagrammatic and partial view of this particular embodiment in a plane which is perpendicular to this observation plane and in which the light from the measurement zone is dispersed conforming to the invention.

FIG. 2B is a diagrammatic and partial view of FIG. 2A where one can see these means of dispersion 18. In the case of FIG. 2B, this device is shown in the direction, or more exactly in the plane which is perpendicular to the straight section for analysis, that is to say in the plane of the dispersion. In the example under consideration, it concerns the plane defined by the axes Z and V.

The light thus dispersed arrives at the sensor 14 and, depending on the spectral composition of the light emitted by the measurement zone considered 4, can range from a beam of red light 20 to a beam of violet light 22 passing through a beam of green light 24.

The image sensor 14 is a bidimensional sensor (comprising for example an array of photo-detectors or a CCD device) and makes it possible to analyse, for a given position of the means of selection, on the one hand in one direction the luminous intensity in function-of the angle θ and on the other hand, in the perpendicular direction, the luminous intensity in function of the wavelength.

Advantageously this sensor 14 is arranged in such a way that its axes correspond to the two directions mentioned above.

When this sensor is a sensor of the CCD type, the dispersion direction, if it is aligned perpendicularly to the columns of this sensor of the CCD type, can make it possible, by using a grouping of charges contained in the pixels (binning), to modulate the sensitivity of the measuring device in function of the wavelength.

The sensor 14 is associated with electronic treatment means 26 envisaged to treat the information collected by the sensor and to associate the spectral response of the measurement zone 4 to each point of the straight section measured. This information is corrected from the actual response of the measuring device by an adapted sampling procedure.

The spectral information thus obtained makes it possible, through weighting by the appropriate coefficients, to calculate the colorimetric co-ordinates for each angle θ considered.

The electronic treatment means 26 are provided with means for displaying the results (not shown).

Figure 2C:
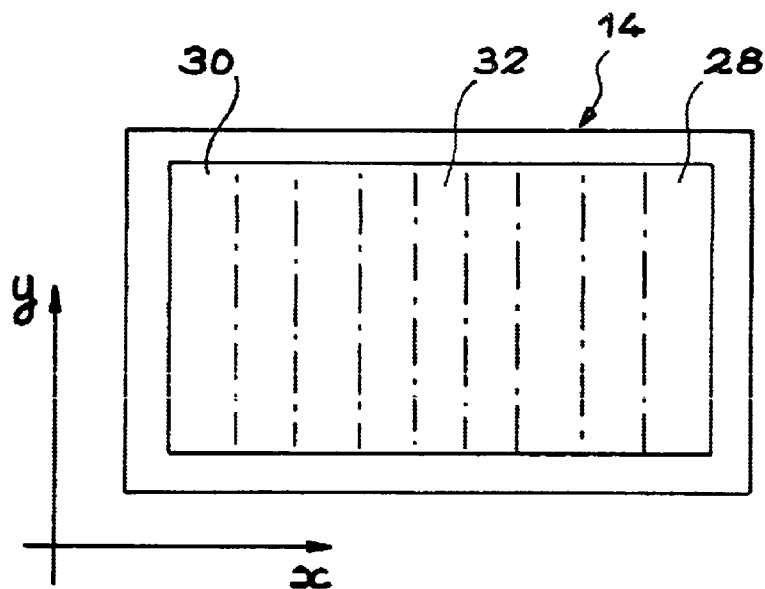
FIG. 2C illustrates diagrammatically the information collected in the plane of the sensor which is part of the device of FIGS. 2A and 2B.

In FIG. 2C the luminous signals collected by the sensor 14 are represented. These signals are represented in the plane of this sensor. The points of this plane are indicated with the aid of two axes x and y. According to the axis y, one finds the data related to the angles θ examined and, along axis x, one finds the data related to the wavelengths.

An analysis of the information collected thanks to the sensor 14 evidently thus gives information according to the various angles of incidence in a straight section, for all the wavelengths of the visible spectrum existing in the light emitted by the measurement zone examined.

The device of FIGS. 2A and 2B thus makes it possible to measure, for any section in the Fourier plane P1, the space and spectral distribution specifications at the same time. In the example considered, this section is a section with constant azimuth.

When the means of selection make it possible to select a straight section of the image of the plane P1, this straight section passing along the optical axis Z of the device (which is the case in the example under consideration), it is possible to turn the object and thus the measurement zone 4 around this optical axis Z in such a way as to be able to study different straight sections of the image contained in plane P1, corresponding to different azimuths, and thus to reconstruct the response of the measurement zone 4 in all the analysis half-space.

Figure 3:
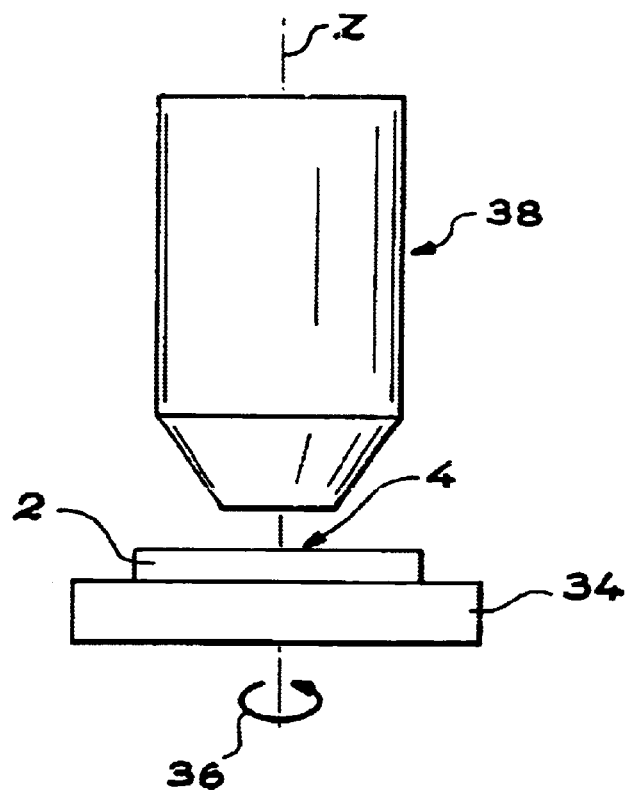
FIG. 3 is a diagrammatic view of the means of rotating an object to be measured in a device conforming to the invention.

This is illustrated diagrammatically in FIG. 3 where one sees the object 2 set on a support 34 provided with means which are symbolised by the arrow 36 and make it possible to turn the object 2 and thus the measurement zone 4 around the optical axis Z of the measuring device 38 which has been described with reference to FIGS. 2A and 2B.

It is also possible to displace the means of selection 16 in the Fourier plane P1 or in the plane P2 mentioned above, in such a way as to reconstruct the behaviour of the measurement zone by scanning for all the angles θ and φ.

Preferably, this displacement is by rotation, around the optical axis Z, of the slit 16 which is placed, as has been seen, in the plane P1 or in the plane P2.

As represented in FIG. 2A, this slit is then made to rotate by adapted mechanical means 40, comprising for example a motor as well as mechanical means for engaging the slit in rotation and the associated electronic control means.

In order to guarantee that the dispersion of the light is orthogonal to the straight section, the means of dispersion 18 must then be linked in rotation (which is possible for the professional) with the means of selection (the slit 16 in the example under consideration).

Preferably, in order to simplify the analysis in the plane of the sensor 14, one adds to the device of FIGS. 2A and 2B a de-rotator device 42 which is placed in the optical path of the light in such a way as to be able to conserve a same orientation for the data collected by sensor 14 whatever the angular position of the slit 16.

This de-rotator device 42 is inserted after this slit 16 so that this de-rotator device can play its role.

When the means of selection (the slit 16 in the example under consideration) are set at the level of plane P1, the de-rotator device 42 is placed between lens 8 and lens 12 or between this lens 12 and the means of dispersion 18.

When the means of selection are placed at the level of plane P2, the de-rotator device 42 is set between these means of selection and the means of dispersion 18.

In the case where this de-rotator device 42 is used, it is no longer necessary to link in rotation these means of dispersion with the means of selection (the slit 16 in the example under consideration) since these means of dispersion maintain a fixed position relative to the sensor 14 as a result of the de-rotation.

These means of light dispersion 18 can be based on the use of one or several diffraction gratings or one or several prisms.

An example of such means of dispersion of light is represented diagrammatically in FIG. 4 and comprises successively a convergent lens 44, a diffraction grating 46 and another convergent lens 48.

FIG. 4 shows the optical axis Z of the measuring device using this example of means of dispersion. It is to be noted that, in this example, the sensor 14 is not on the axis Z.

It is to be noted that FIG. 4 shows the example of means of dispersion in the plane where the dispersion is observed. This plane is perpendicular to the selection plane considered at the exit of the de-rotator device, when the latter is used, or considered at the exit of the slit 16 when this de-rotator device is not used.

It can be seen that the image 50 of the slit 16 is collimated (the divergent beam issuing from this slit being transformed into a beam of parallel rays) by the convergent lens 44.

This beam of parallel rays is sent to the diffraction grating 46 (but a prism of dispersive material could be used instead of this diffraction grating). The beam of parallel rays is then dispersed into a multiplicity of beams whose wavelengths are different.

These beams with different wavelengths are focussed thanks to the other convergent lens 48, the light rays of the same wavelength being focussed at the same point. The image thus obtained is then collected by the sensor 14.

And now to return to the de-rotator device 42.

The aim of this de-rotator device is to carry out a rotation of the axis of an image around its optical axis. Its utilisation in the measuring device described, with reference to FIGS. 2A and 2B, makes it possible to re-align the axes of the image obtained on the sensor 14 whatever the angular position of the means of selection 16.

In practice, to manufacture such a de-rotator device, prisms or mirrors are used.

Various de-rotator devices are known. For example one can consult the book on this subject by W. J. Smith entitled "Modern Optical Engineering". As a purely indicative and non-limiting example, to produce such a de-rotator device one can use prisms of the type Dove, roofless-Abbe or Pechan.

The example of de-rotator device represented diagrammatically in FIG. 5 comprises a prism of the roofless-Abbe type. The path of the light in such a de-rotator device is shown for a beam of parallel rays.

One can also see the (geometrical) axis of rotation z of this de-rotator device which is made to rotate by suitable means, represented by the arrows 51 in FIG. 5. This axis z is also the rotation axis of the means of selection used in the device of FIGS. 2A and 2B.

In the example of FIG. 5, one uses the fact that, if the de-rotator device of this figure is placed in the path of a light beam, the resulting image, obtained at the exit from this de-rotator device, is subjected to a rotation of an angle $2\alpha$ when the de-rotator device goes through a rotation angle $\alpha$. In order to compensate for an azimuth $\phi$ rotation the de-rotator device must thus go through a rotation of an angle $\alpha$ such that $\phi=-2\alpha$.

In the measuring device conforming to the invention of FIG. 2A, the de-rotator device 42 is made to rotate thanks to appropriate means 52, comprising a motor and the associated means of electronic control, in order to compensate the rotation of the plane of selection exactly.

The electronic means of control (not shown), which are associated with the de-rotator device 42, are coupled to the means of electronic control (not shown), which are associated with the means of selection 16.

This coupling is carried out thanks to the means of regulation 54 which ensure that the relation $\phi=-2\alpha$ takes place with the precision required.

The measurement of objects under luminous flux, in particular reflecting objects, can be carried out with the device of FIGS. 2A and 2B by modifying this device as will be explained with reference to FIGS. 6 and 7.

Figure 6:
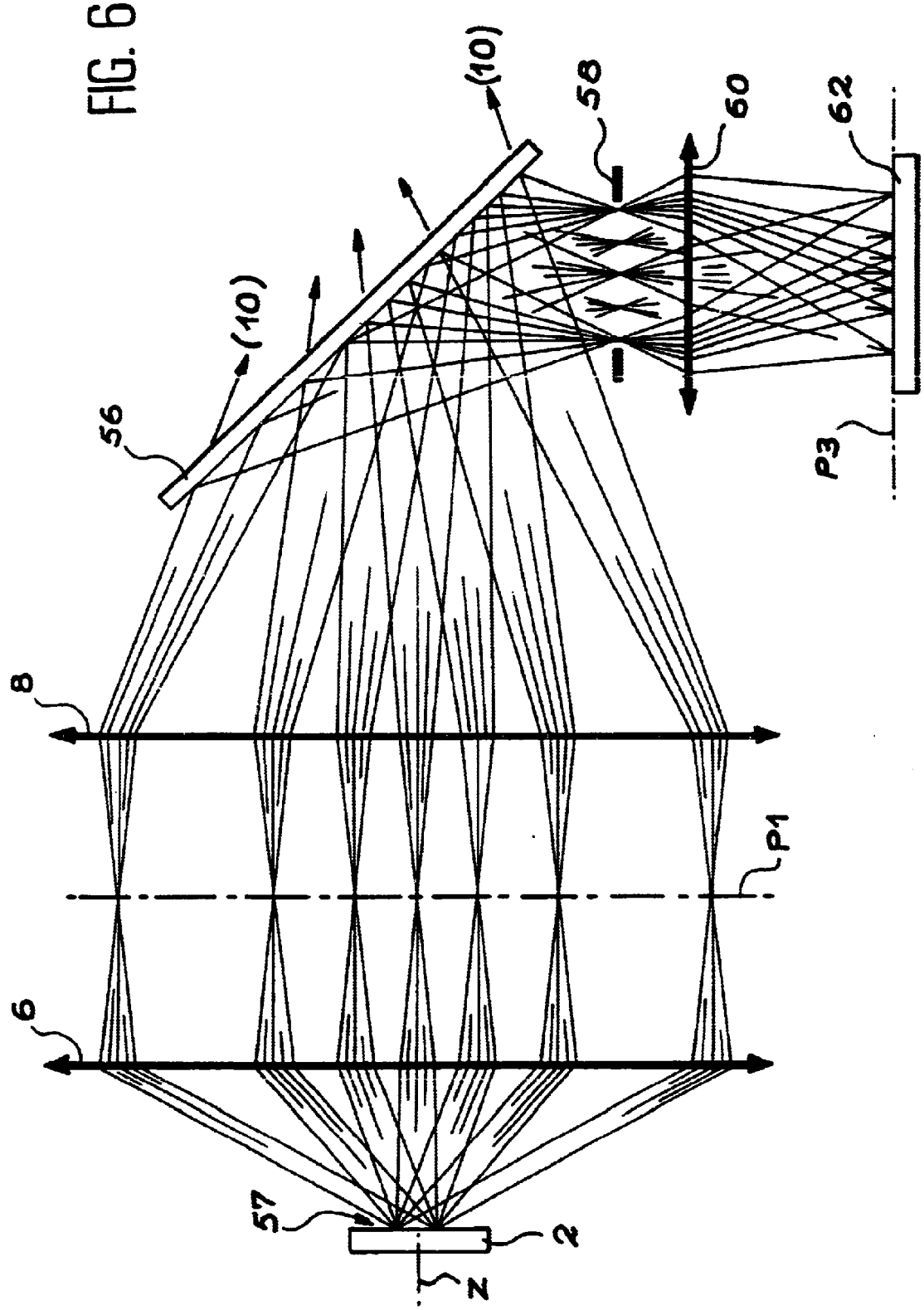
FIGS. 6 and 7 are diagrammatic and partial views of two special embodiments of the invention, both allowing the illumination of an object to measured.
Figure 7:
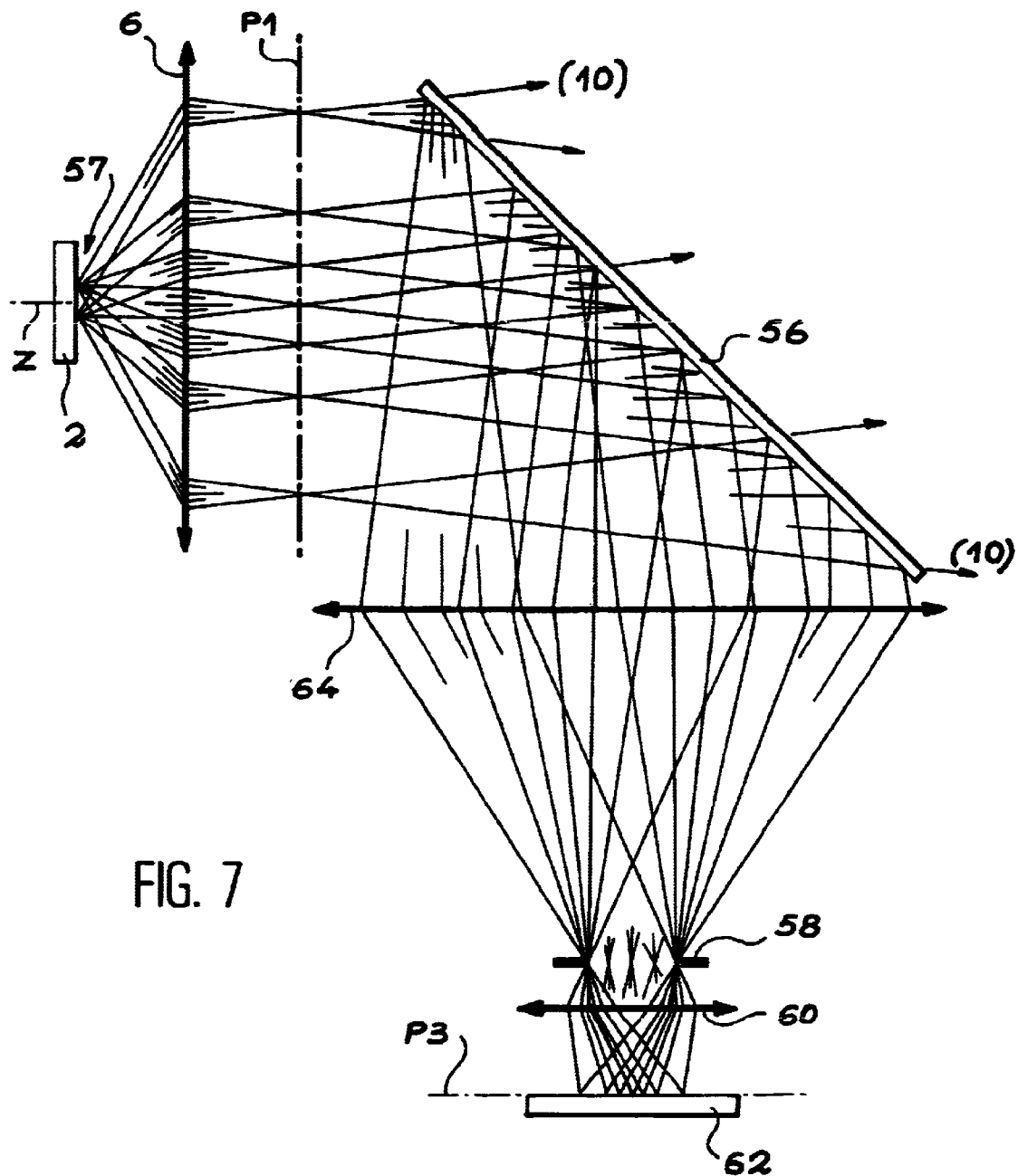

A semi-reflecting device 56 (separator cube or similar) is inserted into the optical path, either after lens 8 (FIG. 6) or between lenses 6 and 8 (FIG. 7).

FIGS. 6 and 7 give details of the operation of the measuring device thus modified, without showing the elements necessary for spectral analysis, so as to simplify the description.

The semi-reflecting device 56 does not prevent propagation of light beams in the direction of the rest of the measuring device. It is therefore possible to make a measurement while still illuminating the object 2.

First of all, let us consider the example of the measuring device of FIG. 6.

One wishes to illuminate a zone 57 of the surface of the object 2, which includes the measurement zone 4 (which was referred to in the description of FIGS. 1 and 2A). A diaphragm 58 with an opening which is preferably circular, conjugated optically with the illumination zone 57 by lenses 6 and 8 (by the intermediary of semi-reflecting means 56) is used to define this zone 57.

The conjugation properties between the diaphragm 58 and the zone of illumination 57 are comparable to those which are applied between the zone 4 and the diaphragm 10, in particular concerning the magnification and the surface compensation which varies as $1/\cos\theta_1$ where $\theta_1$ is then the angle of incidence, on zone 57, of a light beam arriving from diaphragm 58.

A convergent lens 60, placed after the diaphragm 58 in relationship to the semi-reflecting device 56, carries out, in association with the lens 8 (through the intermediary of the semi-reflecting device 56 as shown in FIG. 6), the conjugation between the plane of the Fourier transform P1 and a plane P3.

A luminous source 62 is inserted in this plane P3. This luminous source 62 can be an extended source, a point source placed in any position in the plane P3 or any other source making it possible to reproduce, at the level of the zone of illumination 57, the angular distribution of illumination desired.

Next let us consider the example of FIG. 7 where the lens 8 (not shown) is now on the axis Z on the right of the device 56.

A supplementary convergent lens 64 is then added to the measuring device of FIG. 6, between the semi-reflecting device 56 and the diaphragm 58, as shown in FIG. 7, so as to be able, in association with the lens 6, to carry out the optical conjugation between the zone of illumination 57 and the diaphragm 58.

Let us return to the measuring device of FIG. 2A.

In order to control this measuring device and collect the data, the electronic means 26 for treatment of the signals provided by the sensor 14 and the electronic means 40, 52 and 54 for controlling the means of selection 16 and the de-rotator device 42 are linked to a command unit or a computer of any kind 66.

The measuring device that has just been described fulfills the required function well, which is to obtain rapidly, collectively and simultaneously information about the angular and spectral distribution of each. emitter, reflector or light diffuser.

The capacities of this measuring device can be adapted to the requirements of the users:

One can design a "basic" device conforming to the invention, making it possible to measure in one or several straight sections.

Measurement capacities for samples in reflection mode (under luminous flux) can be added to this basic device.

The use of a de-rotator device makes it possible in addition to analyse all the possible azimuths according to the needs of the users.

For example, in a production unit of emitting or reflecting objects of the type considered here, it is possible to analyse only two directions whose azimuths equal respectively $\phi=0°$ and $\phi=90°$.

I claim:

1. A device for measuring the space distribution of the spectral emission of a measurement zone of an object, comprising:

a first lens to form, in a Fourier plane of the first lens, a first image constituting an optical Fourier transform of the measurement zone;

a first diaphragm;

a second lens set between the first lens and the first diaphragm and co-operating with the first lens so that an opening of the first diaphragm is conjugated optically with the measurement zone by the first and second lenses and so that the measurement zone, when observed through the first diaphragm, has an apparent surface approximately independent of a direction of observation, the first and second lenses having a common optical axis that constitutes an optical axis of the device;

means for selecting a rectilinear portion of the first image following a direction of selection;

means for dispersing light corresponding to the selected portion of the first image;

a bidimensional image sensor, configured to receive the dispersed light and to provide signals representative of the dispersed light; and means for treating the signals, to determine a spectral response of the measurement zone for each point of the rectilinear portion of the first image.

2. Device according to claim 1, wherein the first diaphragm has a circular opening.

3. Device according to claim 1, wherein the means for dispersing light further disperses the light following a dispersion direction perpendicular to the direction of selection.

4. Device according to claim 1, wherein the means for selecting comprises a rectilinear slit formed through a material opaque to light issuing from the object.

5. Device according to 1, wherein the direction of selection passes along the optical axis of the device.

6. Device according to claim 5, further comprising means for rotating the object around the optical axis of the device.

7. Device according to claim 1, further comprising means for displacing the means for selecting, such that the direction of selection scans the first image, the means for selecting thus selecting successive rectilinear portions of the first image.

8. Device according to claim 7, wherein the means for selecting comprises a rectilinear slit formed through a material opaque to light issuing from the object and that defines the direction of selection, the slit passing along the optical axis of the device, wherein the means for displacing includes means for rotating the slit around the optical axis, and wherein the means for dispersing light disperses the light following a direction of dispersion maintained perpendicular to the direction of selection and thus to the slit.

9. Device according to claim 7, wherein the means for selecting comprises a rectilinear slit formed through a material opaque to light issuing from the object and that defines the direction of selection, the slit passing along the optical axis of the device, wherein the means for displacing includes means for rotating the slit around the optical axis, and the device further comprises de-rotator means set between the slit and the means for dispersing light for maintaining constant an orientation of the dispersed light received by the sensor.

10. Device according to claim 9, further comprising a luminous source and semi-reflecting means for reflecting light emitted by the luminous source towards the object to illuminate a zone of the object containing the measurement zone and to let pass light issued from the measurement zone thus illuminated and directed towards the first diaphragm.

11. Device according to claim 10, wherein the semi-reflecting means are set between the second lens and the first diaphragm and the device further comprises:
- a second diaphragm with an opening that defines the illuminated zone, the opening of the second diaphragm being optically conjugated with the illuminated zone by the first and second lenses; and
- a third lens;
- wherein the luminous source is set in a plane conjugated optically with the Fourier plane of the first lens by the second and third lenses.

12. Device according to claim 10, wherein the semi-reflecting means are set between the first lens and the second lens and the device farther comprises:
- third and fourth lenses; and
- a second diaphragm with an opening that defines the illuminated zone, the opening of the second diaphragm being conjugated optically with the illuminated zone by the first and fourth lenses;
- wherein the luminous source is set in a plane conjugated optically with the Fourier plane of the first lens by the third and fourth lenses.

* * * * *